United States Patent [19]

Peyman et al.

[11] Patent Number: 5,516,522
[45] Date of Patent: May 14, 1996

[54] BIODEGRADABLE POROUS DEVICE FOR LONG-TERM DRUG DELIVERY WITH CONSTANT RATE RELEASE AND METHOD OF MAKING THE SAME

[75] Inventors: Gholam A. Peyman; Dachuan Yang; Bahram Khoobehi, all of New Orleans, La.

[73] Assignees: Board of Supervisors of Louisiana State University; Agricultural and Mechanical College, both of New Orleans, La.

[21] Appl. No.: 212,232

[22] Filed: Mar. 14, 1994

[51] Int. Cl.$^6$ .................................................. A61F 2/00
[52] U.S. Cl. .......................... 424/426; 424/422; 424/424; 424/427
[58] Field of Search .................................... 424/422, 424, 424/426, 427

[56] References Cited

U.S. PATENT DOCUMENTS 4,666,704  5/1987  Shalati et al. ............................ 424/426
5,324,519  6/1994  Dunn et al. ............................. 424/426

Primary Examiner—Melvyn I. Marquis
Assistant Examiner—D. Aylward
Attorney, Agent, or Firm—Haverstock, Garrett & Roberts

[57] ABSTRACT

A biodegradable porous drug delivery device for controllably releasing a pharmacological agent is disclosed which comprises a hollow tube closed at both ends having an interior surface and an exterior surface, the tube formed of a mixture of polycaprolactone and a pore-creating agent, the tube further comprising channels formed between the interior surface and the exterior surface and a pharmacological agent filled into the hollow tube for controllable release through the channels of the tube. Methods of manufacturing the biodegradable porous drug delivery device are also disclosed.

16 Claims, 6 Drawing Sheets

BIODEGRADABLE POROUS DEVICE FOR LONG-TERM DRUG DELIVERY WITH CONSTANT RATE RELEASE AND METHOD OF MAKING THE SAME

BACKGROUND OF THE INVENTION

This invention relates to biodegradable porous reservoir devices for long-term drug delivery, and in particular to biodegradable porous reservoir devices which provide controlled and sustained therapeutic drug levels for extended periods of time.

Currently there are many methods for developing effective delivery devices used in medical applications for delivering drugs or other agents. An ideal pharmaceutical delivery system provides the drug only when and where it is needed and at the appropriate concentration to obtain the designed therapeutic effect. Such methods include biodegradable systems and diffusional delivery systems. Biodegradable systems include a polymer matrix having a therapeutic agent or drug incorporated therein. The biodegradable system releases the drug as the polymer matrix degrades. Usually the polymer matrix contains hydrolytic or enzymatic label bonds on its main molecular chain and as the polymer erodes due to the cleavage of these bonds the encapsulated therapeutic agent is exposed and released. The most often used biodegradable polymers are poly(lactic acid), poly(glycolic acid), poly(ortho ester), and polyanhydrids and their copolymers. The important advantage to using such biodegradable systems is that surgery is not required to remove the waste delivery device after the drug administration period due to the degradation of the polymer matrix. Although biodegradable systems are useful, one disadvantage associated with their use is that the polymers do not deliver the drug at a constant rate and for a long enough period to achieve the required therapeutic effect.

Diffusional delivery systems can be divided into either matrix types or reservoir types. Diffusional delivery systems are based on non-biodegradable polymer materials. The matrix type typically has the therapeutic agent dissolved or mixed with the polymer matrix. The therapeutic agent then diffuses through the polymer matrix. The matrix type system has the advantage that it is easy to make and presents no danger of rupturing or leaking. However, one disadvantage associated with its use is that the drug release may not be constant. The reservoir type is composed of an inner cavity that contains the therapeutic agent which in turn is surrounded by a semipermeable membrane that controls the flow or release of the therapeutic agent. The reservoir type system has the advantage that it provides a zero-order or constant rate of release. However, several disadvantages include the possibility of leaks or ruptures, it is expensive to make, and additional surgery is required to remove the empty carrier.

With respect to ocular structures, currently vitreoretinal diseases are inadequately treated either by repeated topical application of ophthalmic drops or by frequent subconjunctival or intravitreal drug injection. Furthermore, depending on the extent and severity of the ocular disease, systemic drug delivery treatment is occasionally being used. Topical drug-delivery treatment severely limits the access of almost all drugs into intraocular structures. This is due to the heterogeneity of corneal structure being composed of a lipophilic epithelial component (barrier to polar drugs) and a hydrophilic stroma component (barrier to lipophilic drugs). It has been determined that in successful cases less than 8% of the total drug that is being applied topically is able to reach the sites of action in the vitreoretinal structures. On the other hand, the systemic drug-delivery method while effective for transport of lipophilic drugs into vitreoretinal structures is not effective for delivery of hydrophilic drugs from the blood side into the retina and vitreous. The delivery of hydrophilic drugs is severely hindered because of the presence of an impermeable blood-retinal barrier to charged, hydrophilic agents. Furthermore, systemic administration of drugs with narrow therapeutic index often results in a general systemic toxicity. Because of these limitations in delivering the drugs into their sites of action in the vitreoretinal structures, Peyman and coworkers pioneered the method of intravitreal drug administration in the early 1970s in order to achieve therapeutically effective concentration of drugs in the vitreous and retina (Arch. Ophthalmol. 92:42–47, 1974: and Arch. Ophthalmol. 91:416–418, 1974). Unfortunately, the successful treatment of most of the vitreoretinal diseases requires repeated intravitreal drug injection in order to maintain adequate drug concentration in the vitreous for a desired period of time. Even if repeated intravitreal drug administration into an already compromised eye may improve the outcome of certain ocular conditions, the intravitreal strategy suffers from several problems including increased risk of ocular infection, intraocular hemorrhage, and retinal and lens damage. Moreover, the initial drug peak level achieved immediately after an intravitreal bolus injection may result in ocular toxicity, further complicating the disease process. In an attempt to reduce or even eliminate these serious problems while improving the efficacy of ophthalmic agents for treatment of vitreoretinal diseases, several other strategies have subsequently been developed.

One such strategy, which attempts to improve the bioavailability of drugs at the receptor sites in the vitreous and retina, is a drug-delivery system with sustained-release feature. This drug-delivery system includes microspheres (Wood Int. J. Pharmaceutics 7:1–18, 1980). Microspheres of biodegradable polymers have been utilized to prolong the bioavailability of ophthalmic drugs in the retina and vitreous cavity. The use of biodegradable polymers, based on lactic and glycolic acids, in general surgery has clearly demonstrated the biocompatiblility and usefulness of this class of polymers. As such, this information has further encouraged their use as biodegradable carrier in the form of microspheres for controlled drug delivery. Microsphere-incorporated drugs have been shown to prolong the half-life of certain drugs, thus, eliminating the need for repeated intravitreal injection, thereby lowering the risk of complications. In other studies, microspheres have been shown to reduce the toxicity associated with some drugs.

Although kinetic studies indicate that microsphere-drug delivery systems may be useful for sustaining the release of lipophilic drugs, there are inherent problems with these drug delivery techniques regarding their use for intraocular applications. It is also known that microsphere-drug delivery systems have a tendency to diffuse and disperse throughout the vitreous humor when injected into the vitreous. This property causes vitreous haziness and thus, blurred vision occurs for at least 2 to 3 weeks following intravitreal injection. This problem not only complicates the evaluation of the vitreoretinal status in this critical moment of the treatment course, but also precludes the patient to see until the complete resorption of the drug formulation. Nevertheless, the successful formulation of such drug delivery system provides therapeutic drug levels for only 2 to 3 weeks, and when necessary, repeated intravitreal injections are required.

Because of these limitations, alternative methods have been pursued.

The need for a well tolerated, biodegradable porous reservoir type drug device for long-term drug delivery is even more pressing in that numerous posterior segment eye diseases would be treated if such a drug device would be available. Such a biodegradable porous drug device would be superior to the existing delivery systems described above because it would not be dispersed throughout the vitreous and it would not require surgical removal following its insertion into the eye. An ideal biodegradable porous drug delivery device should be composed of an inert, biodegradable carrier with one or more pharmacologically active agents, and it should exhibit a slow-release feature for a desired period of time without causing any adverse effects on ocular structures. Such a biodegradable porous drug delivery device will be inserted by physicians into a patient's eye for successful treatment of certain intraocular conditions such as: 1) following vitreoretinal surgeries which predispose the eye to a subsequent development of proliferative vitreoretinopathy (PVR), including long-standing retinal detachments, giant retinal tears, traumatic eye injuries with or without involving foreign bodies, tractional detachments in uveitis, endophethalmitis, or diabetic retinaopathy; 2) complications of immunodeficiency syndrome where viral and other pathogenic organisms affect the retina including CMV retinitis and other viral retinitis; 3) when intraocular pressure is compromised which may consequently cause loss of vision, such as macular edema; 4) inhibition and prevention of neovascularization; and 5) for prevention of cellular proliferation in fistulating glaucoma procedures where removal of vitreous is indicated such as aphakic glaucoma, which does not respond to current therapy. For all these reasons, development of a safe, effective intraocular biodegradable drug device for treatment of posterior segment eye disorders is warranted. Intraocular drug delivery devices with sustained-release feature can have potential clinical applications for effective treatment of posterior segment (vitreoretinal) diseases because most of the vitreoretinal disorders require long-term therapy.

The advantages of such an intraocular biodegradable drug device may include the following: 1) it would eliminate the need for repeated intravitreous drug injection because the device provides drug release for long-term therapy; 2) it would reduce or even abolish drug toxicity associated with the therapeutic levels of antiproliferative and antiviral agents because of its slow-release feature; 3) it would not diffuse or disperse throughout the vitreous cavity, thus, it would not cause vitreous cloudiness; 4) the device can be modified with respect to the rate and duration of drug release, as such, the device satisfies the requirements of a specific therapy, i.e., PVR (2 to 3 months treatment course), CMV retinitis (lifetime treatment), and macular edema (more than 3 months treatment); 5) the device does not require subsequent surgical removal from the eye since it gradually degrades while it is releasing its content; and 6) the drug device can be formed in any desired dimensions and configuration which may be deemed necessary.

SUMMARY OF THE INVENTION

A biodegradable porous drug delivery device for controllably releasing an effective amount of a pharmacological agent comprises a hollow tube closed at both ends having an interior surface and an exterior surface, the tube formed of polycaprolactone and further comprising channels formed between the interior surface and the exterior surface and a pharmacological agent filled into the hollow tube for controllable release through the channels of the tube.

Accordingly, it is an object of the present invention to provide a biodegradable porous drug device for long-term delivery of therapeutic agents or drugs in the body to treat disorders of the body.

It is another object of the present invention to provide a biodegradable porous drug delivery device which combines the features and advantages of both the biodegradable matrix drug delivery systems and the reservoir type drug delivery systems.

It is another object of the present invention to provide a biodegradable porous intraocular drug delivery device which combines the features and advantages of both the biodegradable matrix drug delivery systems and the reservoir type drug delivery systems.

It is an object of the present invention to provide a biodegradable porous drug device for long-term drug delivery which does not impair or damage ocular structures.

It is a further object of the present invention to provide a therapeutic drug level in the vitreous for a duration greater than 3 months for the treatment of eye disorders.

A still further object of the present invention is to provide a biodegradable porous drug device for treatment of disorders of the eye which has all the advantages of both a matrix drug delivery device and a reservoir drug delivery device.

These and other objects and advantages of the present invention will become apparent after considering the following detailed specification in conjunction with the accompanying drawings, wherein:

DETAILED DESCRIPTION OF THE PREFERRED EMBODIMENT

As described above, one of the major limiting factors in successful treatment of diseases is the inability to deliver an effective concentration of therapeutic agents to the diseased area and for a long or extended period of time. Thus, a drug delivery device with sustained release feature may be useful for effective treatment of diseases. The present invention is therefore based upon the need and great interest to develop methods and compositions for applications which obviate the limitations of currently available modes of therapies.

Figure 1:
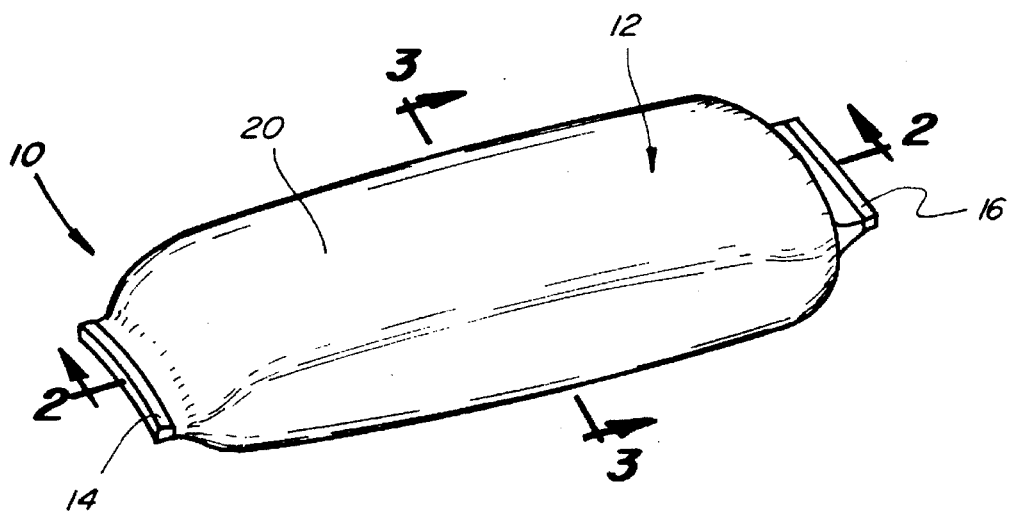
FIG. 1 is a perspective view of a biodegradable porous device for long-term drug delivery constructed according to the present invention.
Figure 2:
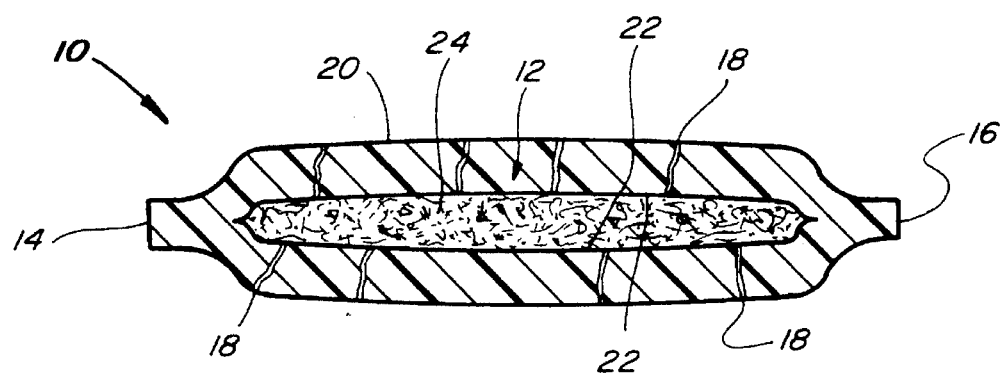
FIG. 2 is a cross-sectional view of the biodegradable porous device shown in FIG. 1 taken along the plane of line 2—2 of FIG. 1.
Figure 3:
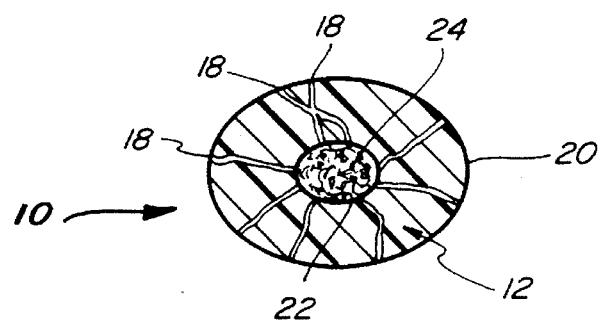
FIG. 3 is a cross-sectional view of the biodegradable porous device shown in FIG. 1 taken along the plane of line 3—3 of FIG. 1.

Referring now to the drawings, wherein like numerals refer to like items, number 10 identifies a preferred embodiment of the biodegradable porous device for long-term drug delivery which is constructed according to the present invention. With reference now to FIGS. 1, 2, and 3, the device 10 comprises a hollow tubular section 12 having a pair of sealed ends 14 and 16. The tubular section 12 has holes, pores, or channels 18 formed therein between an exterior surface 20 and an interior surface 22. A pharmacological agent 24, such as a hydrophilic pharmaceutical agent for long-term duration, is filled in the hollow tubular section 12. The biodegradable polymer which is used for the porous device 10 is polycaprolactone (PCL). This material is chosen due to its long-term biodegradable behavior, it being non-toxic, and having a low melting point. PCL is an FDA approved commercial medical material. PCL having a viscosity-average molecular weight (M$\eta$) from 5,000–100,000 may be used with the preferred range being 30,000–60,000. The selection of molecular weight is dependent upon the expected life time of the delivery device. For example, the higher the molecular weight the longer the life time of the device. The formed channels 18 may take on any pattern such as straight from the interior surface 22 to the exterior surface 20 or even a criss-cross pattern as illustrated in FIG. 3. The method of forming the channels will be explained in detail below.

Figure 4:
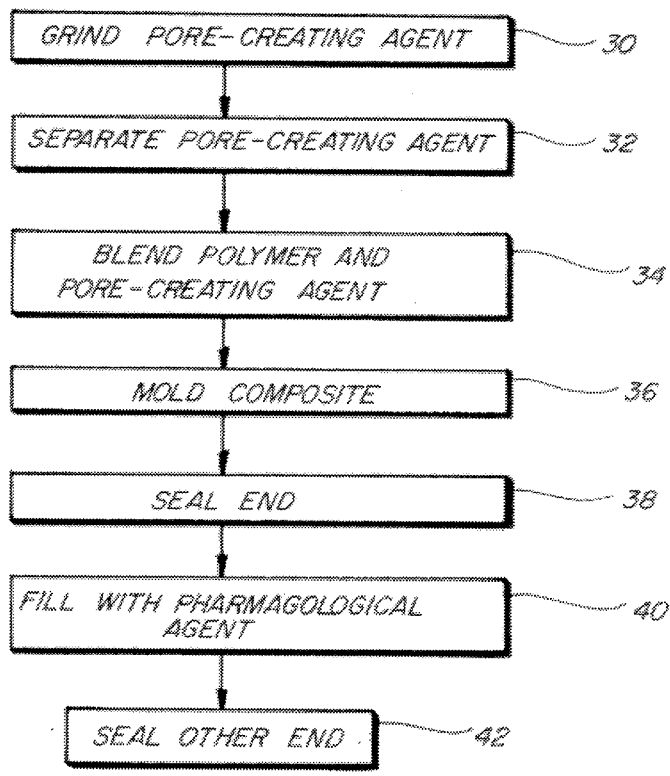
FIG. 4 generally depicts the method of preparing the biodegradable porous device of the present invention.

FIG. 4 depicts a method for preparing the biodegradable drug delivery device 10. The first step in preparing the device 10 is to grind up a pore-creating agent such as an inert, non-toxic, and water soluble solid particle. The pore-creating agent is ground up by using a ceramic mortar or a mechanical mill. This step is indicated by the block numbered 30. The non-toxic water soluble solid particle used as the pore-creating agent can be inorganic salts or organic salts, or any low molecular weight polymeric compounds. The water soluble particles or pore-creating agent can be any non-toxic, powderable substance with the preferred compounds being small molecule salts such as potassium chloride (KCl), sodium chloride (NaCl), sodium phosphate ($Na_3PO_4$), potassium acetate ($CH_3COOK$), poly(acrylic sodium), and poly(vinyl alcohol) and mixture thereof. Other examples of suitable pore-creating agents include a metal inorganic salt with a halide, sulphate, phosphate as counterions, an inorganic salt such as potassium acetate, a water soluble polymer having low molecular weight such as the above mentioned poly(acrylic sodium) and poly(vinyl). The next step, block 32, is to separate the ground up pore-creating agent by using a sieve into the various fine sizes of the particles. The particles can be any fine size with the sizes being between 100–400 mesh and the preferred range of sizes being between 140–325 mesh. Polycaprolactone and the pore-creating agent are then blended together. The weight percent of pore-creating agent in the polymer composite is preferable in the range of 0% to 70.0% or more, with the preferred range being about 5.0% to 30.0%. The PCL and the pore-creating agent are blended in a solid container and then slowly heated by a carefully controlling the temperature between 60° C. to 180° C. The preferred temperature range being between 100° C. to 140° C. An inert gas, such as nitrogen, helium, or argon, may be used to protect the thermal decomposition of the PCL. After the mixture becomes a high viscous liquid, a strong mechanical stirrer is used to help mix into a homogeneous mixture. A vacuum line with lower than 750 mmHg pressure is used to expel the residual gas in the mixture to reduce air bubbles in the walls of the end product. The blending step is illustrated by block 34. As represented by block 36, the viscous liquid is then cast in a mold to form a hollow tube. However, the porous reservoir device of the present invention can be manufactured in a wide variety of shapes and sizes to deliver therapeutic agent to different environments of medical applications. For example, the porous reservoir device can be a buccal and oral device, vaginal and intrauterine device of cylinder, bullet, elliptical, circular, bulbous, bow or any other shape or form that may be placed in the living body environment. The porous reservoir device for ocular applications may be of any geometric shape for implantation in the culde sac such as the shapes of ellipsoid, bean, banana, circular, rectangular, doughnut, crescent, and half-ring shape. The dimensions of the ocular devices may vary according to the size of the eye with such dimensions generally having a length of 1–20 mm, width of 1–10 mm or diameter of 1–10 mm, and a wall thickness of 0.1–2 mm. The molded device is then cut to length, if required, and one end of the device is sealed by a melting process. This step is depicted by block 38. The next to last step in the manufacturing process, as illustrated by block 40, is to fill the capped hollow tube with a pharmacological or therapeutic agent. As will be explained further herein, the therapeutic agents delivered by the device of the present invention may have hydrophilic properties. The therapeutic agent may be antibiotics, antivirus, antifungal, antiinflecte, antiinflammate, antiproliferatives, antineoplastic, antiparasitic, and diagnostic drugs. It may also be a protein drug, enzyme, growth factor or hormone. Examples of typical therapeutic agents are 5-fluorouracil, ganciclovir, foscarnet, daunomycin, and 5-carboxyfluorescein. These biologically active substances can be administered in any convenient manner such as in powder form, liquid form, or ointment form. However, the preferred form is powder. The subsequent forming of the porous reservoir device by heat method. The last step, as depicted by block 42, is to seal the other end of the tube. When closing or sealing the end of the device, as shown in block 42, care must be taken to seal the end at a low enough temperature which will not damage the therapeutic agent which has previously been filled into the device. One or more suitable noses having a tiny hole may be made on the end of the device to provide the site for supporting a surgical suture, if required.

Once the device 10 is manufactured according to the above described method it may be inserted into the body for treatment purposes. Once in the body, the device 10 comes into contact with body fluids and the pore-creating agent within the device 10 dissolves to create the pores or channels 18 within the device 10. Once the pores 18 are created the device 10 releases the pharmacological agent through the pores or channels 18 at a constant or zero-order rate. Additionally, because the device 10 is biodegradable, the device 10 degrades within the body and there is no need for further surgery to remove any waste. The device 10 combines the features and advantages of both the biodegradable matrix drug delivery systems and the reservoir type drug delivery systems. The pore size and pore density in the device 10 have a direct effect on the release rate of different therapeutic agent. In accordance with the present invention, a porous reservoir device having large pore size is used for therapeutic agents having big molecular volume which requires higher release rates. Larger sized particles of pore-creating agent blended with the polymer PCL creates bigger pores than smaller sized particles. Additionally, higher loading of the pore-creating agent yields higher pore density or more channels in the polymer matrix.

Biocompatible porous drug delivery devices will be useful as intraocular implants for treatment of vitreoretinal diseases. The drug device comprises a biocompatible, bioerodible polycaprolactone polymer having conduits or channels formed therein and one or more therapeutic agents which may be released over a desired period of time at a therapeutically effective level within the vitreoretinal structures. The drug device may be used immediately following vitreoretinal surgeries, which predispose the eye to a subsequent development of proliferative vitreoretinopathy, to provide therapeutic drug levels in the vitreous cavity for up to three or more months to effectively prevent and/or suppress abnormal cellular proliferation. In a more chronic condition, for example cytomegalovirus retinitis associated with AIDS syndrome, the drug device may be used to provide therapeutic drug levels of antiviral agents for a prolonged period of time for controlling the symptoms of the infection. In this manner, the drug device may be used continuously as needed for the duration of the lifetime of the patient. Where the device is used for treatment of intraocular hypertension, such as macular edema, the delivery device may be used to provide therapeutic drug levels of carbonic anhydrase inhibitors or other antihypertensive agents in the vitreous cavity and, in particular, the retina for an extended period of time. In all these situations, the bioavailability of therapeutic agents can be improved significantly by the drug device since the drug will be available at the sites of action. Further, potential side effects of the drug are reduced or even abolished by controlling the rate of drug release.

The therapeutic component of the intraocular drug device for PVR treatment will be anitproliferative agents. The drug delivery device can be prepared in any desired dimensions and configuration to include one or more drugs at therapeutically effective concentrations. Any pharmacologically active antimetabolites, antibiotics, and steroids with antiproliferative and/or anti-inflammatory properties may be used in the formulation. Drugs of particular interest for treatment of PVR include antimetabolites, such as 5-fluorouracil, 5-fluorouridine 5-monophosphate, 5-fluoro-2'-deoxyuridine, and cytarabine; anticancer agents, such as daunomycin (or its hydrochloride salt), doxrubicin (or its hydrochloride salt), adriamycin (or its hydrochloride salt), mitomycin, bleomycin, retinol and retinoic acids; steroids, such as cortisone (or its acetate), hydrocortisone (or its acetate/cypionate/succinate/sodium phosphate), prednisone, prednisolone (or its acetate/tebutate/sodium phosphate), 6 alpha-methyl-prednisolone (or its acetate/succinate), fluorocortisone, fluorometholone, beclomethasone, betamethasone (or its acetate/benzoate/dipropionate/valerate/sodium phosphate), dexamethasone (or its acetate/sodium phosphate), medrysone, paramthasone (or its acetate), and triamcinolone (or its acetonide/diacetate/hexacetonide). Drugs of interest for inhibition of neovascularization include alpha-interferon, gama-interferon, amiloride, and steroids with antiproliferative effect.

The active components of the intraocular drug device for CMV retinitis and other viral retinitis will be antiviral agents. The drug delivery device can be prepared to include one or more drugs at a therapeutically effective concentration. Any pharmacologically active antiviral, antibiotics, and steroids separately or in combinations may be used in the formulation. Drugs of particular interest for treatment of CMV retinitis include antivirals, such as, ganciclovir, fuscarnet, acyclovir, vidarabine, trifluorouridine, idoxuridine, Ribavirin, and zidovudine. The active component of the intraocular drug delivery device for ocular hypertension will be carbonic anhydrase inhibitors, such as acetazolamide, methazolamide, dichlorphenamide, diamox or a derivative thereof, and MK-417.

Other pharmacological agents may be employed in the drug device for a variety of purposes. In addition to the active ingredient, diluents, buffering agents and preservatives may be employed. The preservatives may include benzalkonium chloride, antioxidants, such as ascorbic acid, sodium bisulfite, parabens, benzyl alcohol and with or without essential vitamins. The drug device may contain sodium chloride, glucose, calcium, magnesium, glycerin, hydrochloric acid and/or sodium hydroxide to adjust osmolarity and pH during manufacturing procedure. These agents may be added in amounts of from about 0.001 to about 5%.

Additionally, it is to be understood that by controlling the size of the fine particles which are incorporated within the polycaprolactone various porous devices having different pore or channel sizes may be produced. Also, by controlling the ratio of fine particles incorporated within the polycaprolactone various porous devices having different pore or channel densities may be manufactured. In some instances different pharmacological agents may be filled in the porous device, This results in a single application of treatment instead of two or more. The release rates of the different pharmacological agents may be varied if necessary. For example, one agent incorporated at one end of the porous device may be allowed to be released quickly by fabricating one end of the porous device with a high channel density. The other end of the porous device could have a lower channel density and the pharmacological agent at that end would be released slowly.

The following are examples of tests which have been conducted on various porous reservoirs which have been made according to the present invention.

EXAMPLE 1

Polycaprolactone (PCL) was chosen as the initial material to make the composite with the pore creating agent. The PCL used in this example has a viscosity average molecular weight ($M\eta$) and four different samples of PCL were used such as PCL1 having $M\eta$ of 60,000; PCL2 having $M\eta$ of 30,000; PCL3 having $M\eta$ of 22,000; and PCL4 having $M\eta$ of 10,000. The PCL1 was a commercial product purchased from Aldrich (U.S.A.) and a purification process was used before blending with the pore-creating agent to remove any contaminations including the residue catalyst. The PCL1 was dissolved in tetrahydrofuran (THF) to a concentration of 20 wt %. A great amount of methanol or cold water was added to participate the PCL1 then a great amount of distilled water was used to wash the participate. The product was then dried under vacuum condition at below 40° C. The low molecular weight PCL (PCL2, PCL3, and PCL4) is not commercially available and was prepared from PCL1 by the acidic hydrolysis degradation method developed by D. Yang, an inventor herein, and described in D. Yang, "Low molecular weight polycaprolactone and poly(DL-lactide) prepared by hydrolysis and their application as biodegradable carriers for drug delivery", ARVO 65th annual meeting, Sarasota, Fla., May 1993. By controlling the catalyst and reaction condition, a series of PCL with different viscosity-average molecular weight were prepared, such as PCL2, PCL3, and PCL4. The measurement of molecular weight was determined by the intrinsic viscous method in the CHCl$_3$ solvent at 25° C., the k and α constants were determined from the literature, in particular, Koleske, J. V., "Polymer Blends", Vol. 2, Academic Press, New York, 1978, p. 369.

The pore-creating agents used in this example were inorganic metal salt such as sodium chloride (NaCl), potassium chloride (KCl), the organic metal salt such as potassium acetate (CH$_3$COOK). These were all analytical reagent without further treatment. All these substances were hard solid particles and were ground to fine powder by using a ceramic mortar. The powder was divided through a group of standard sieves.

A 30 ml glass round bottle was used to blend 5.0 g of each of the different viscosity-average molecular weight PCL and pore-creating agent. A rubber stopper with an insert glass tube connected to a vacuum line was used to cover the 30 ml bottle. The mixture was slowly heated to below its decomposition temperature on a hot plate whiles at the same time stirring the mixture. The temperature was controlled by using a silicon oil bath. To reduce the gas bubble in the late forming of the reservoir device, the vacuum line was used to pull out any residual gas in the liquid mixture. As discussed previously, an inert gas may be used to avoid thermal decomposition. A homogeneous composite is obtained by this procedure and this composite is used in forming the reservoir device.

Various composites of PCL and pore-creating agent were prepared by changing the PCL molecular weight, the pore-creating agent type, size, and loading. Such properties are listed in Table I.

TABLE I

| Composite No. | PCL (M | Pore-creating Agent | Size (mesh) | Loading (wt %) | Pore Observation |
|---|---|---|---|---|---|
| I01 | 60,000 | no | no | no | no |
| I02 | 60,000 | KCl | <325 | 10 | + |
| I03 | 60,000 | KCl | <325 | 20 | ++ |
| I04 | 60,000 | KCl | <325 | 30 | +++ |
| I05 | 60,000 | KCl | <325 | 50 | +++++ |
| I21 | 60,000 | NaCl | <325 | 10 | + |
| I22 | 60,000 | NaCl | <325 | 20 | ++ |
| I23 | 60,000 | NaCl | <325 | 30 | +++ |
| I24 | 60,000 | NaCl | <325 | 40 | ++++ |
| I31 | 30,000 | CH$_3$COOK | <140 | 10 | ++ |
| I32 | 30,000 | CH$_3$COOK | <140 | 30 | ++++ |
| I33 | 30,000 | CH$_3$COOK | <140 | 50 | +++++ |
| I41 | 60,000 | PVA | <140 | 30 | +++ |

The mark (+) in Table I represents an increase of pores developed in the composite samples.

Figure 5:
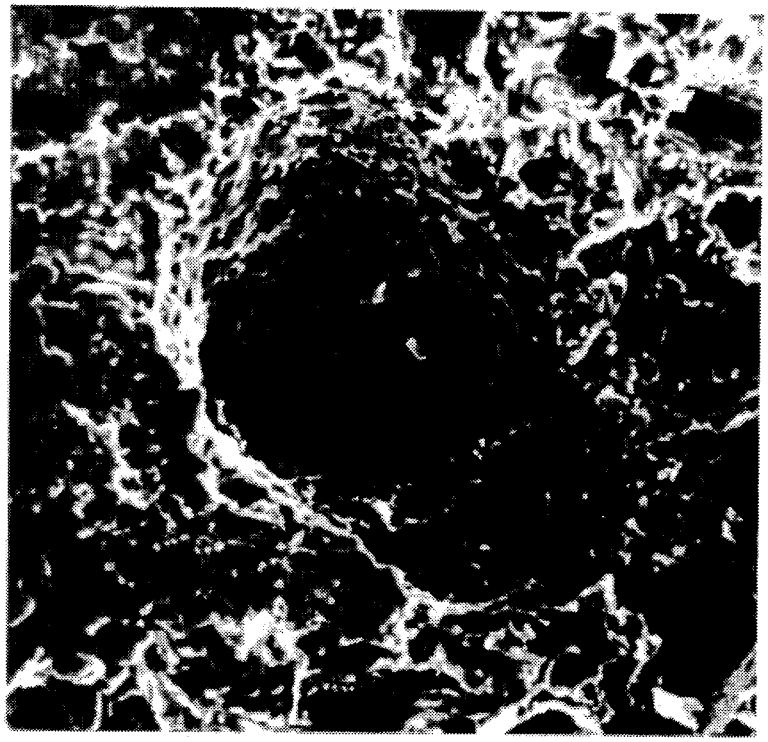
FIG. 5 is a scanning electron microscope photograph of the morphology of the pore created in the biodegradable porous device

The scanning electronic microscope (SEM, DSM 950, Zeiss) was used to observe the pore and channel development in the composite after the specimen plate contacted with an aqueous media (incubated in 0.1M neutral phosphate buffer solution) for 24 hours. A number of pores can be found across the section of the sample plate with the pore density being increased when the loading of pore-creating agent was higher than 30 wt % by the dense neighbor pores joined together. Bigger size pore-creating agent caused the rougher pore structure compared to the smaller size particles and bigger size pore-creating agent created more channels in the same loading composite. Referring to the PCL without any loading of pore-creating agent, the SEM photo showed a solid texture without any pore and channel. The molecular weight of PCL had not affected to the occurrence of pores and channels but brought a change of mechanical property when the molecular weight (Mη) of PCL was lower than 20,000. The composite had a bad mechanical strength and was brittle. The type of pore-creating agent was not showing influence to the pore structure and morphology. Since the role of pore-creating agent presented was only by its physical volume that occupied a definitive space in the composite and its water soluble feature disappeared after contact with the penetrated water. FIG. 5 shows a typical SEM photo that demonstrated the morphology of the pore created in the PCL composite.

The composite containing pore-creating agent particle was formed further by vacuum pressure molding method to form a tubular shape. In this example, the glass mold was used with one termination connected to a three-way valve that can be switched between the vacuum line and pressure air line. By the use of vacuum, the high viscous liquid of the composite was pulled up along the glass tube to a height then the valve was switched to the pressure air line. The pressure air line pushed most of the composite liquid down and left some of it attached on the wall of the glass tube. The mold was quickly moved to a cool water bath while keeping the air flowing. The liquid composite condensed on the wall and a tubular reservoir was formed. The glass tube was then broken to remove the formed tubular reservoir device. The wall thickness of the tubular reservoir device as between 0.30 to 0.35 mm and the inner diameter was between 1.4 to 2.4 mm.

Cytomegalovirus (CMV) retinitis is a main reason for the cause of visual loss in patients having acquired immunodeficiency syndrome (AIDS). The reported number of new CMV retinitis cases in the United States in 1992 alone was 20,000 to 30,000. Ganciclovir (9-(1,3-dihydroxy-2-propoxymethyl) guanine, monosodium salt) is an effective antiviral drug developed by Syntex. However, it requires weekly intravenous injection to maintain long term therapy. A long term sustained release device made by non-biodegradable polymer, crosslinked poly(vinyl alcohol), was reported by T. J. Smith, P. A. Pearson, D. L. Blandford, et al., "Intravitreal sustained-released ganciclovir", Arch. Ophthamol., Vol. 110, p. 225, 1992.

In this example, the long term ganciclovir delivery devices were prepared using the tubular reservoirs made in Example I. Specifically, the tubular reservoir samples used were I01, I03, I04, and I05 with the pore-creating agent comprised from 0 wt % to 50 wt %. All tubular samples were cut to 8.0 mm long with one side closed mechanically by a clamp. This side was then heated locally using a hot plate until the side melted and formed a smooth edge. The top was about 1.0 mm long and a tiny hole was made for carrying the surgical suture. The other side was used to fill the device with powder ganciclovir (which was purchased from Syntex). This end was then sealed by clamping it and carefully melting it by using a hot plate as discussed above. The final device had a length of 4.0 mm and a diameter of 2.0 mm. Eight ganciclovir devices were made at four different release rates as follows: IIA1 (ganciclovir contained 8.1 mg), IIA2 (8.9 mg), IIB1 (8.3 mg), IIB2 (8.3 mg), IIC1 (8.3 mg), IIC2 (8.2 mg), IID1 (4.3 mg), and IID2 (7.1 mg).

Ganciclovir released from the above long-term delivery devices was investigated in vitro. The test was carried out in a glass vial with 2.0 ml, 0.1M, pH 7.4, phosphate buffer solution (PBS) in the shaking water bath at a temperature of 37° C., and at oscillations of 18 cycles per minute. At the interval period, the PBS media was replaced by fresh one and the collected buffer comprised Ganciclovir was quantitatively measured by the UV-VIS spectrophotometer (DU 7400, Beckman) at the 252 nm absorbent wavelength. At least once a week, the one day release media was collected for the determination of daily release level.

Figure 6:
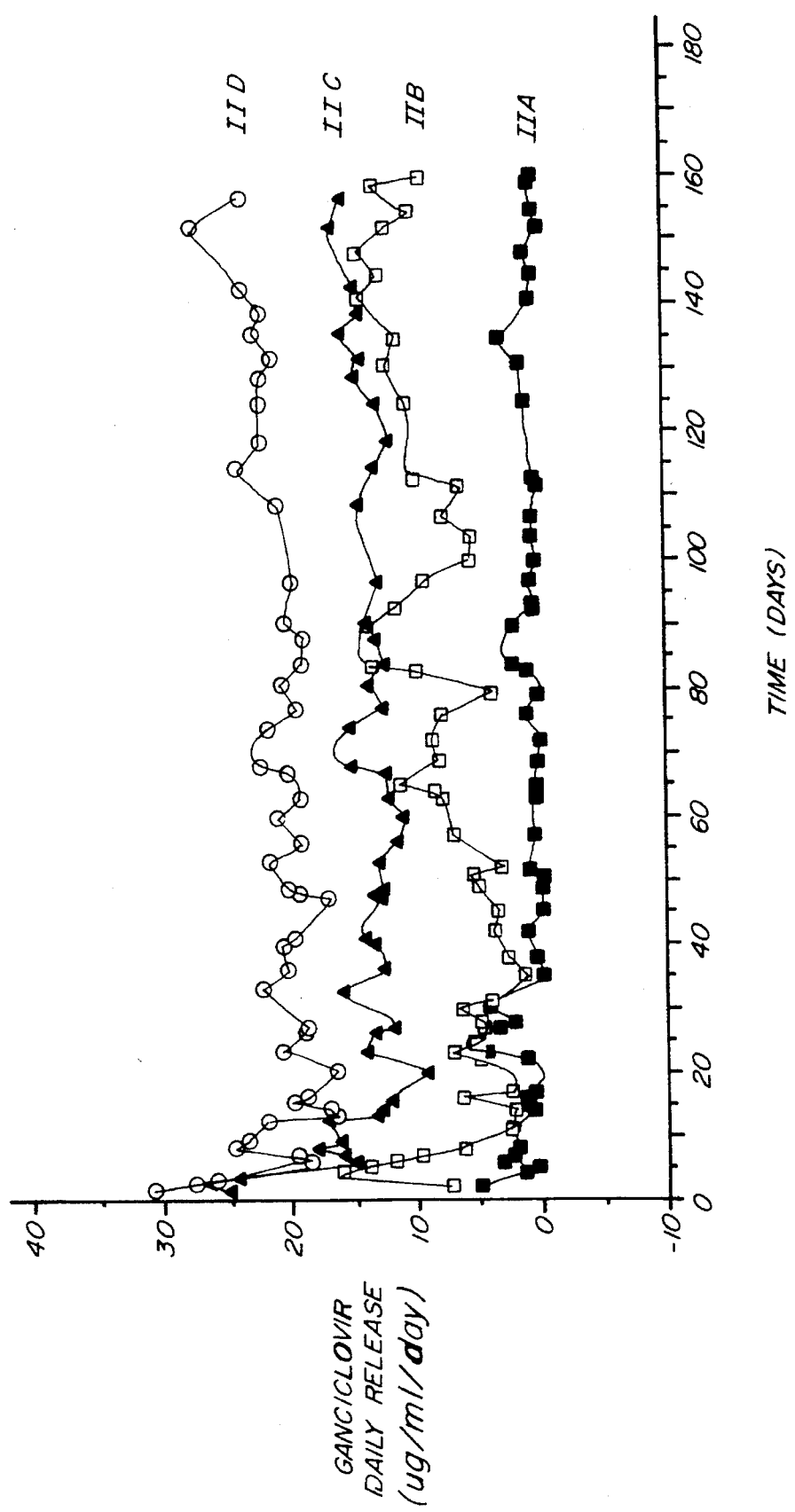
FIG. 6 is a graph of samples of biodegradable porous devices showing daily release of ganciclovir versus days.
Figure 7:
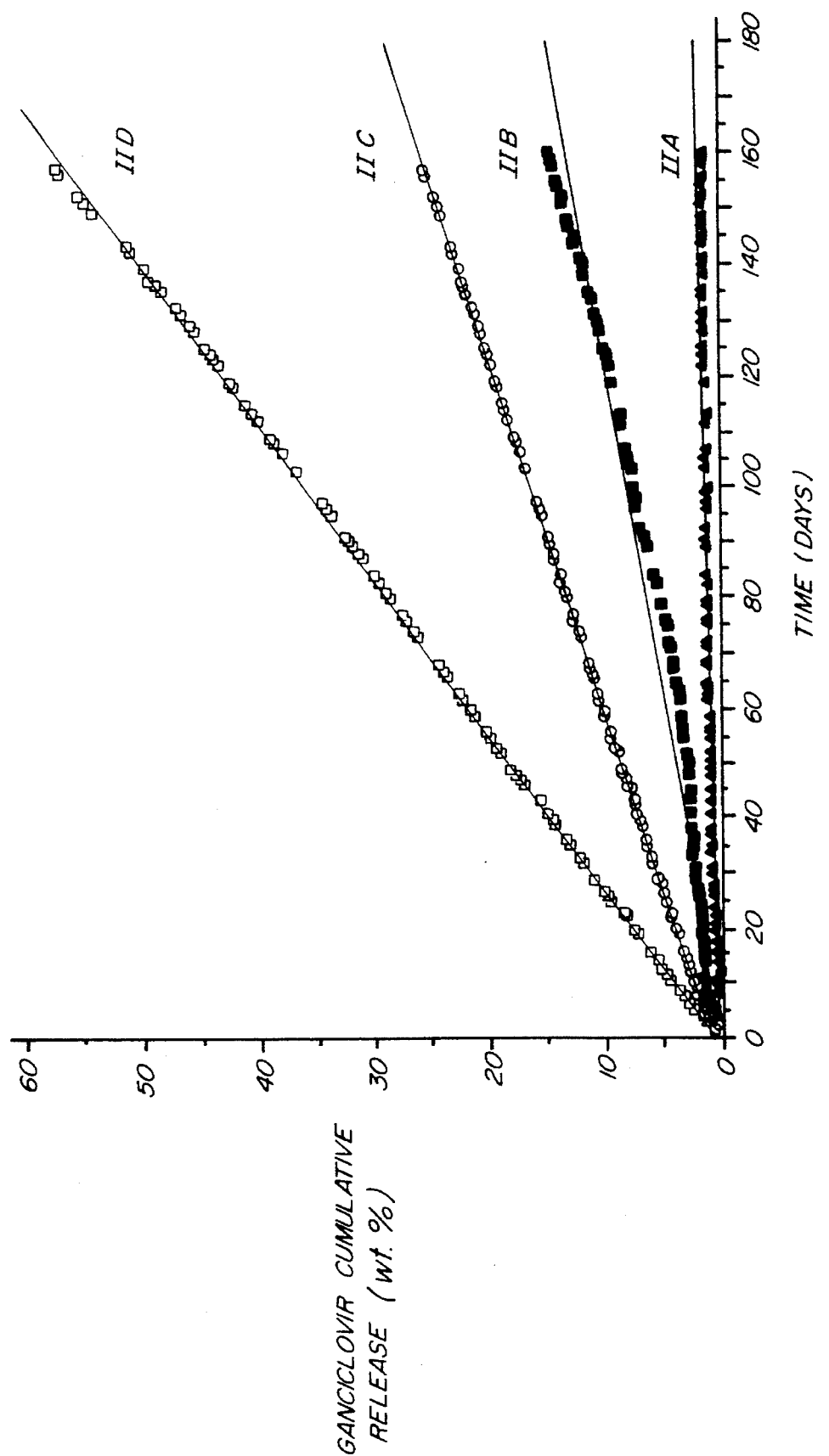
FIG. 7 is a graph of samples of biodegradable porous devices showing the daily release of ganciclovir versus days.

The release process of ganciclovir almost immediately began after the in vitro test at a very constant rate and at four different daily release levels. No initial drug burst phenomenon was observed, this was observed in the conventional monolithic drug device. According to the results as illustrated in FIGS. 6 and 7, devices IIA (without any pore-creating agent loaded, as level 1) released only 1.69 wt % its original ganciclovir content during 160 days at a daily rate of about 1.5 µg/ml/day; devices IIB (with 20 wt % pore-creating agent loaded, as level 2) released 14.7 wt % ganciclovir for the 160 days duration at a rate of about 8.0 µg/ml/day; devices IIC (with 30 wt % pore-creating agent loaded, as level 3) released 25.6 wt % ganciclovir for the same period at a rate of about 13.0 µg/ml/day; and devices IID (with 50 wt % pore-creating agent loaded, level 4) released 57.3 wt % ganciclovir for the duration at a rate of about 20 µg/ml/day.

After the period of 160 days incubation process, some of the devices displayed an indication of surface change. The straight curves in FIG. 7 represent the perfect zero-order kinetic process. However, IIA had neglected release because of the absence of pore-creating agent. The results in this example provide an ideal long-term controllable ganciclovir release pattern.

EXAMPLE III

In this example the antiviral drug 5-fluorouracil (2,4-dihydroxy-5-fluoro-pyrimidine) (purchased from Sigma) was chosen as a drug for long-term therapeutic effect. The long-term 5-fluorouracil delivery devices were prepared using the same technique as described in Example II, except the in preparing the porous reservoir sodium chloride (NaCl) was used as the pore-creating agent. In particular, the tubular reservoirs which were used were I01, I02, I03, and I24 with a pore-creating agent loaded from 0 wt % to 40 wt %, as indicated in Table I. All tubular samples were cut to the same size of 8.0 mm long and one end was closed by heating. The 5-fluorouracil powder was filled densely within the tubular reservoirs and sealed as set out in detailed with reference to Example II. In total, six devices were prepared in the four groups as IIIA1, IIIA2, IIIB1, IIIB2, IIIC1, and IIID1.

The in vitro release test of the 5-fluorouracil delivery devices was carried out in 3.0 ml PBS buffer, shacked in the water bath at 37° C. The amount of released 5-fluorouracil based on one or several day periods was detected by the UV spectrum method at the absorbent peak wavelength of 267 nm.

Figure 8:
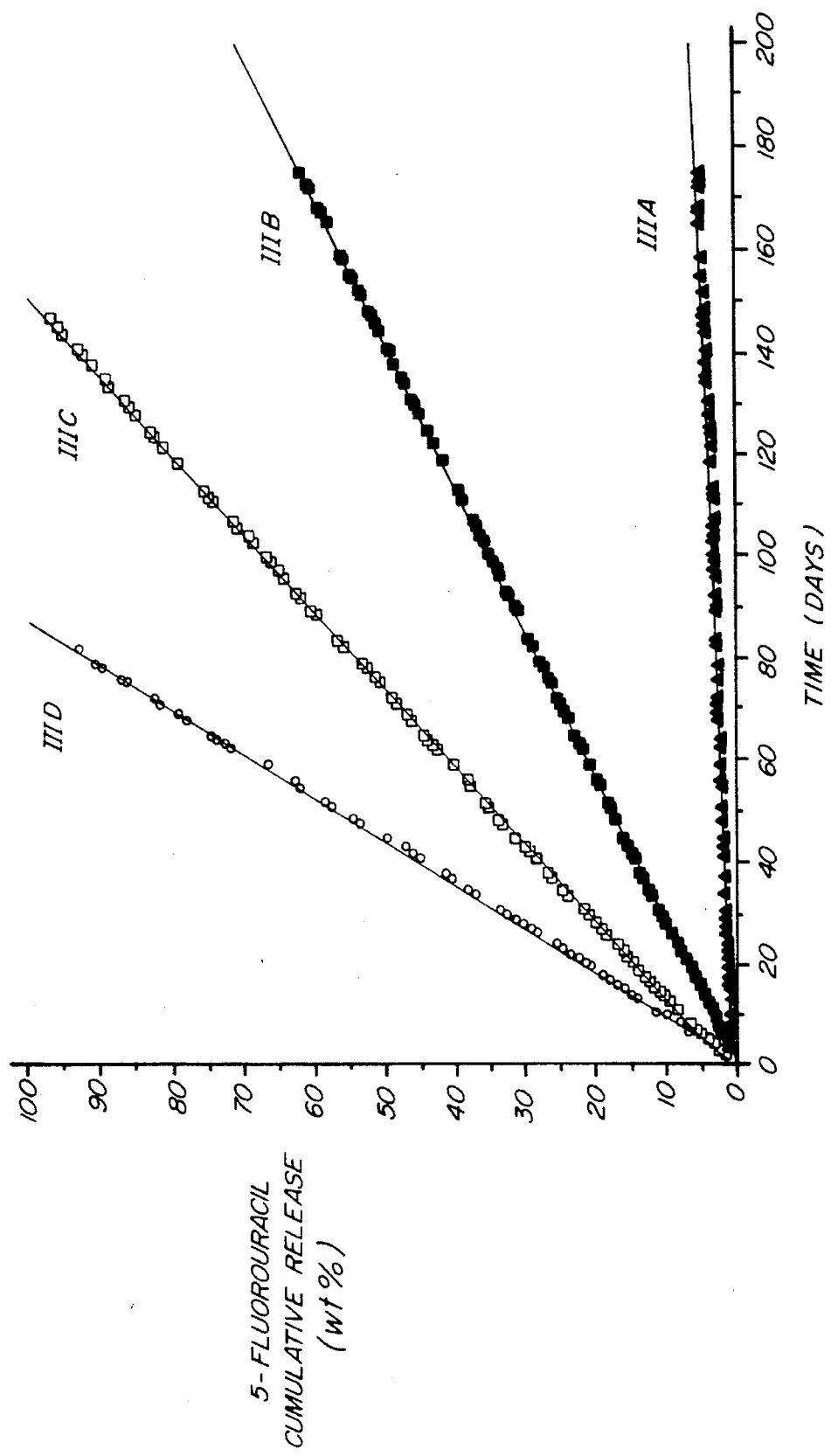
FIG. 8 is a graph of samples of biodegradable porous devices showing the release of 5-Fluorouracil versus days.

The released amount of 5-fluorouracil from the delivery devices was plotted as the cumulative release (wt %) against time (days), as is depicted in FIG. 8. The IIIA samples demonstrated a very low release rate, about 2.0 µg/ml/day, and lower than 5.0 wt % of 5-fluorouracil was detected for the 180 days period. This is due to 0 wt % pore-creating agent in the device. With the presence of pore-creating agent in the reservoir device, the IIIB group sample having 10 wt % pore-creating agent loaded showed a daily release of 22.5 µg/ml/day, the cumulative release of 180 days period was 61.5 wt %, and it is theorized that it would take over 120 days to finish all the release of the 5-fluorouracil at this release rate. For the group of samples IIIC having 30 wt % pore-creating agent loaded, the higher pore density and the assuming channel helped to increase the release rate. A total of 96.5 wt % of carried 5-fluorouracil was checked during the 180 days period at a constant rate of about 43.0 µg/ml/day. For the IIID group of samples having 40 wt % of pore-creating agent loaded the release rate was 65.0 µg/ml/day, over 92 wt % of carried 5-fluorouracil was released for the 80 days duration. All of the devices in the test exhibited a well shape after 180 days of incubation and no evidence of drug burst effect was found.

EXAMPLE IV

Example III was repeated using the porous reservoir to deliver hydrophilic fluorescent dye 5-carboxyfluorescein, which was purchased from Sigma. This drug is an important dye tracer that is used in eye disease diagnostics. The traditional administration of this dye cannot achieve high intraocular concentration because of the limited penetration through the cornea or sclera.

The 5-carboxyfluorescein delivery device was prepared using the same procedure as discussed with reference to Example II, except the porous reservoir was made using an organic salt potassium acetate ($CH_3COOK$) as the pore-creating agent. The tubular reservoirs used were the previously stated I01, I31, I32, and I33 with the pore-creating agent loaded from 0 wt % to 50 wt %, as listed in Table I. Six devices were prepared in the four groups as IVA1, IVA2, IVB1, IVB2, IVC1, and IVD1.

The devices released 5-carboxyfluorescein at four different levels in the in vitro test using a 3.0 ml PBS buffer as the media at 37° C. and shaking condition. The released 5-carboxyfluorescein was analyzed by using an UV photometer.

Figure 9:
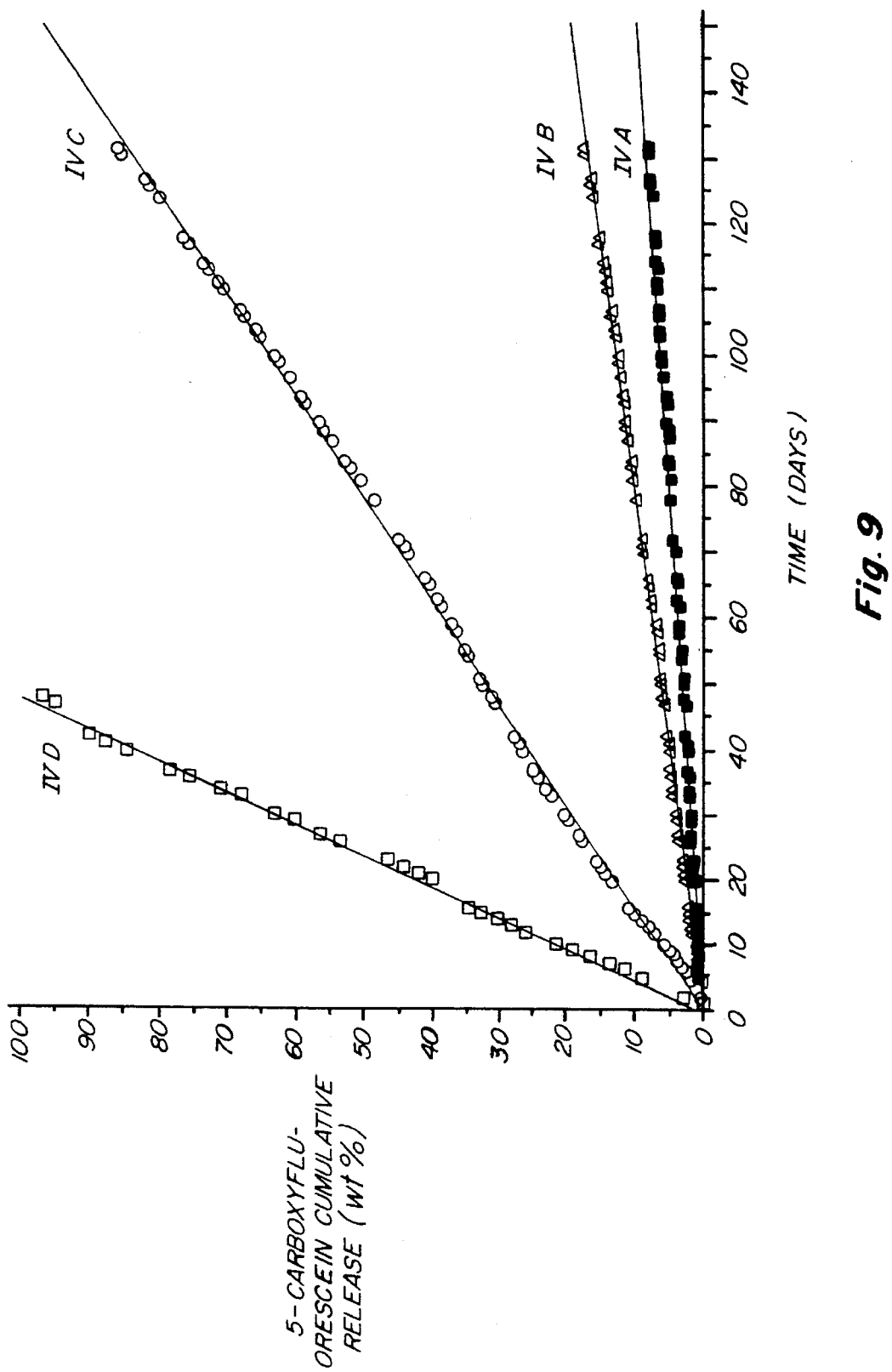
FIG. 9 is a graph of samples of biodegradable porous devices showing the release of 5-Carboxyfluorescein versus days.

The release results of over three months are illustrated in FIG. 9 and a straight line was obtained as the cumulative release (wt %) plotted against time in days. The first group sample IVA showed a very low release rate with about a 3.0 µg/ml/day was observed due to the non-pore structure of the reservoir devices. The cumulative release of 132 days was 8.0 wt % of its carried amount. The IVB samples showed an increased release in view of the role of 10 wt % pore-creating agent. The daily release rate of the dye was about 8.0 µg/ml/day and the 132 days cumulative release was 17.4 wt %. With the pore-creating agent loaded at 30 wt % the increase of pore and the action of the channels increased the daily release rate of 5-carboxyfluorescein in the IVC samples to about 38.4 µg/ml/day. The aggregate release rate of 132 days was 86.1 wt %. When the composition of pore-creating agent in the reservoir devices IVD reached 50 wt % the daily release rate of 5-carboxyfluorescein became about 90 µg/ml/day and all of the 5-carboxyfluorescein was released in one and a half months.

The surface of all 5-carboxyfluorescein release devices presented a visible color of yellow that developed from light to deep with the increase of the pore-creating agent. It is similar to the inorganic metal salts as the pore-creating agent and the organic metal salt in this example played the same role to provide pores and channels in the reservoir device.

From all that has been said, it will be clear that there has thus been shown and described herein a biodegradable porous drug delivery device which fulfills the various objects and advantages sought therefor. It will be apparent to those skilled in the art, however, that many changes, modifications, variations, and other uses and applications of the subject biodegradable porous drug device are possible and contemplated. All changes, modifications, variations, and other uses and applications which do not depart from the spirit and scope of the invention are deemed to be covered by the invention, which is limited only by the claims which follow.

What is claimed is:

1. A biodegradable porous drug delivery device for controllably releasing an effective amount of a pharmacological agent, the device comprising:

a hollow tube having an interior surface and an exterior surface and a first end and a second end, the tube formed of a mixture of polycaprolactone and a pore-creating agent and further having channels formed between the interior surface and the exterior surface; and a pharmacological agent filled into the hollow tube for controllable release through the channels of the tube, the first end being heat sealed prior to the pharmacological agent being filled into the hollow tube and the second end being heat sealed after the pharmacological agent is filled into the hollow tube.

2. The device of claim 1 further comprising a second pharmacological agent filled into the hollow tube for controllable release through the channels of the tube when the device is inserted into a body.

3. The device of claim 1 wherein the pore-creating agent is an inert water soluble material.

4. The device of claim 3 wherein the channels are formed when the pore-creating agent comes into contact with an aqueous solution to dissolve the pore-creating agent within the device.

5. The device of claim 3 wherein the inert water soluble material comprises particles and the particles are of the same size to form the channels of the same size.

6. The device of claim 3 wherein the inert water soluble material comprises particles and the particles are of different sizes to form channels of different sizes.

7. The device of claim 1 wherein the density of the channels is greater with the greater amount of pore-creating agent incorporated with the polycaprolactone.

8. The device of claim 1 wherein the polycaprolactone has a viscosity-average molecular weight between 11,000 to 100,000.

9. The device of claim 1 wherein the density of the channels is small with the smaller amount of pore-creating agent incorporated with the polycaprolactone.

10. The device of claim 1 wherein the tube is formed by heating the mixture at a temperature between about 60° C. and about 180° C.

11. The device of claim 10 wherein the preferred temperature range of heating the mixture is between about 100° C. and about 140° C.

12. The device of claim 1 wherein the polycaprolactone has a preferred viscosity-average molecular weight in the range between 30,000 and 60,000.

13. The device of claim 1 wherein the weight % of pore-creating agent to polycaprolactone is in the range of 0%–70%.

14. The device of claim 13 wherein the weight % of pore-creating agent to polycaprolactone has a preferred range of 5%–30%.

15. The device of claim 1 wherein the pore-creating agent has a mesh size between about 100 and 400.

16. The device of claim 15 wherein the preferred range for the mesh size is between about 140 and 350.

* * * * *